US00PP13350P2

(12) United States Plant Patent
van Rijn

(10) Patent No.: US PP13,350 P2
(45) Date of Patent: Dec. 10, 2002

(54) ANTHURIUM PLANT NAMED 'SUNNY LOVE'

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 09/968,322

(22) Filed: Sep. 30, 2001

(51) Int. Cl.[7] ..... A01H 5/00

(52) U.S. Cl. ..... Plt./365

(58) Field of Search ..... Plt./367, 365

(56) References Cited

PUBLICATIONS

UPOV–ROM GTITM Computer Database 2001/06, GTI Jouve Retrieval Software, citation for 'Sunny Love'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Anthurium plant named 'Sunny Love', characterized by its upright and somewhat outwardly spreading plant habit; freely clumping growth habit; durable dark green leaves; light orange red and green-colored spathes with yellow-colored spadices that are positioned above and beyond the foliage on strong and erect scapes; freely flowering habit; and good inflorescence longevity.

2 Drawing Sheets

BACKGROUND OF THE INVENTION

Botanical classification: *Anthurium andreanum.*
Variety denomination 'Sunny Love'.

The present invention relates to a new and distinct cultivar of Anthurium plant, botanically known as *Anthurium andreanum,* and hereinafter referred to by the name 'Sunny Love'.

The new Anthurium is a naturally-occurring whole plant mutation discovered by the Inventor in a controlled environment in Schipluiden, The Netherlands in 1999. The new Anthurium was discovered as a single plant within a population of plants of the *Anthurium andreanum* cultivar Orange Love, disclosed in U.S. Plant Pat. No. 11,117.

Asexual propagation of the new cultivar by meristem culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Sunny Love. These characteristics in combination distinguish 'Sunny Love' as a new and distinct cultivar:

1. Upright and somewhat outwardly spreading plant habit.
2. Freely clumping growth habit.
3. Durable dark green leaves.
4. Light orange red and green-colored spathes with yellow-colored spadices that are positioned above and beyond the foliage on strong and erect scapes.
5. Freely flowering habit
6. Good inflorescence longevity..

Plants of the new Anthurium are most similar to plants of the parent, the cultivar Orange Love. In side-by-side comparisons conducted in Schipluiden, The Netherlands, plants of the new Anthurium differed from plants of the cultivar Orange Love primarily in spathe color as plants of the new Anthurium have light orange red and green-colored spathes whereas plants of the cultivar Orange Love have solid orange-colored spathes.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the cultivar Sunny Love that was about two years old.

The photograph at the top of the second sheet comprises a close-up view of typical inflorescences of 'Sunny Love'.

The photograph at the bottom of the second sheet comprises a close-up view of the upper surface of a typical mature leaf of 'Sunny Love'.

DETAILED BOTANICAL DESCRIPTION

In the following description, color references are made to The Royal Horticultural Society Colour Chart, 1995 edition, except where general terms of ordinary dictionary significance are used. The following observations and measurements describe two-year old plants grown in 17-cm containers in Schipluiden, The Netherlands, in a glass greenhouse with an average day temperature of 25° C. and an average night temperature of 19° C.

Botanical classification: *Anthurium andreanum* cultivar Sunny Love.

Parentage: Naturally-occurring whole plant mutation of *Anthurium andreanum* cultivar Orange Love, disclosed in U.S. Plant Pat. No. 11,117.

Propagation:

*Method*.—By meristem culture.

*Time to develop roots on a meristem-cultured plant*.—Summer: About 70 days at 24° C. Winter: About 84 days at 21° C.

*Root description*.—Strong fleshy roots.

Plant description:

*Plant shape*.—Upright and somewhat outwardly spreading plant habit, inverted triangle, symmetrical.

*Growth habit*.—Freely clumping, bushy and dense growth habit. Appropriate for 17 to 35-cm containers. Vigorous.

*Plant height*.—About 50 to 70 cm.

*Plant diameter or spread*.—About 75 cm.

*Crop time*.—About 10 months are usually required from planting of young plants to finished plants in a 17-cm container.

*Foliage description*.—Quantity per plant: About 80. Length: About 10 to 20 cm. Width: About 7 to 12 cm. Shape: Cordate. Apex: Aristate. Base: Cordate. Margin: Entire. Texture: Leather; glabrous. Venation pattern: Pinnate. Color: Young leaves, upper surface: 137A. Young leaves, lower surface: Between 144A and 146C. Mature leaves, upper surface: Closest to 147A. Mature leaves, lower surface: 144A. Venation, upper surface: 146C. Venation, lower surface: 146D. Petiole: Length: About 20 to 30 cm. Color: 144B. Geniculum length: About 2 to 3 cm. Geniculum color: 144B.

Inflorescence description:

*Inflorescence arrangement*.—Spathes with spadices held above and beyond the foliage. Flowering structures arise from leaf axils. Freely and continuous flowering year-round; typically more than 30 inflorescences per plant at one time.

*Inflorescence longevity*.—Inflorescences last about six weeks under winter conditions and about three months under summer conditions; persistent.

*Spathe*.—Length: About 9 to 13 cm. Width: About 12 to 14 cm. Shape: Broadly deltoid to cordate. Apex: Aristate. Base: Auriculate; lobes not overlapping. Margin: Entire. Texture: Leathery; glabrous; slight blistering. Color: When opening, front and back surfaces: Center, 183A; towards lateral margins and lobes, close to 143A; glossy. Fully developed, front surface: Center, 41A; towards lateral margins and lobes, 144A; glossy. Fully opened, back surface: Center, 41D; towards lateral margins and lobes, 145B; glossy.

*Spadix*.—Length: About 2 to 5 cm. Diameter: About 1 cm. Shape: Columnar. Cross section: Rounded. Longitudinal axis: Erect. Color: Immature: 144A. Mature: 8D; towards apex, 13A.

*Flowers*.—Quantity per spadix: Numerous, about 200. Shape: Rounded. Diameter: About 1 mm, maximum.

*Reproductive organs*.—Androecium: Pollen color: Close to 158B. Gynoecium: Stigma shape: Ovoid.

*Scape*.—Length: About 40 to 55 cm. Aspect: Strong and erect. Color: 144A overlain with anthocyanin, 178A.

*Seed/fruit*.—Seed/fruit development on plants of the new Anthurium has not been observed to date.

Disease/pest resistance: Under commercial conditions, plants of the new Anthurium have not ben observed to be resistant to pathogens or pests common to Anthurium.

It is claimed:

1. A new and distinct cultivar of Anthurium plant named 'Sunny Love', as illustrated and described.

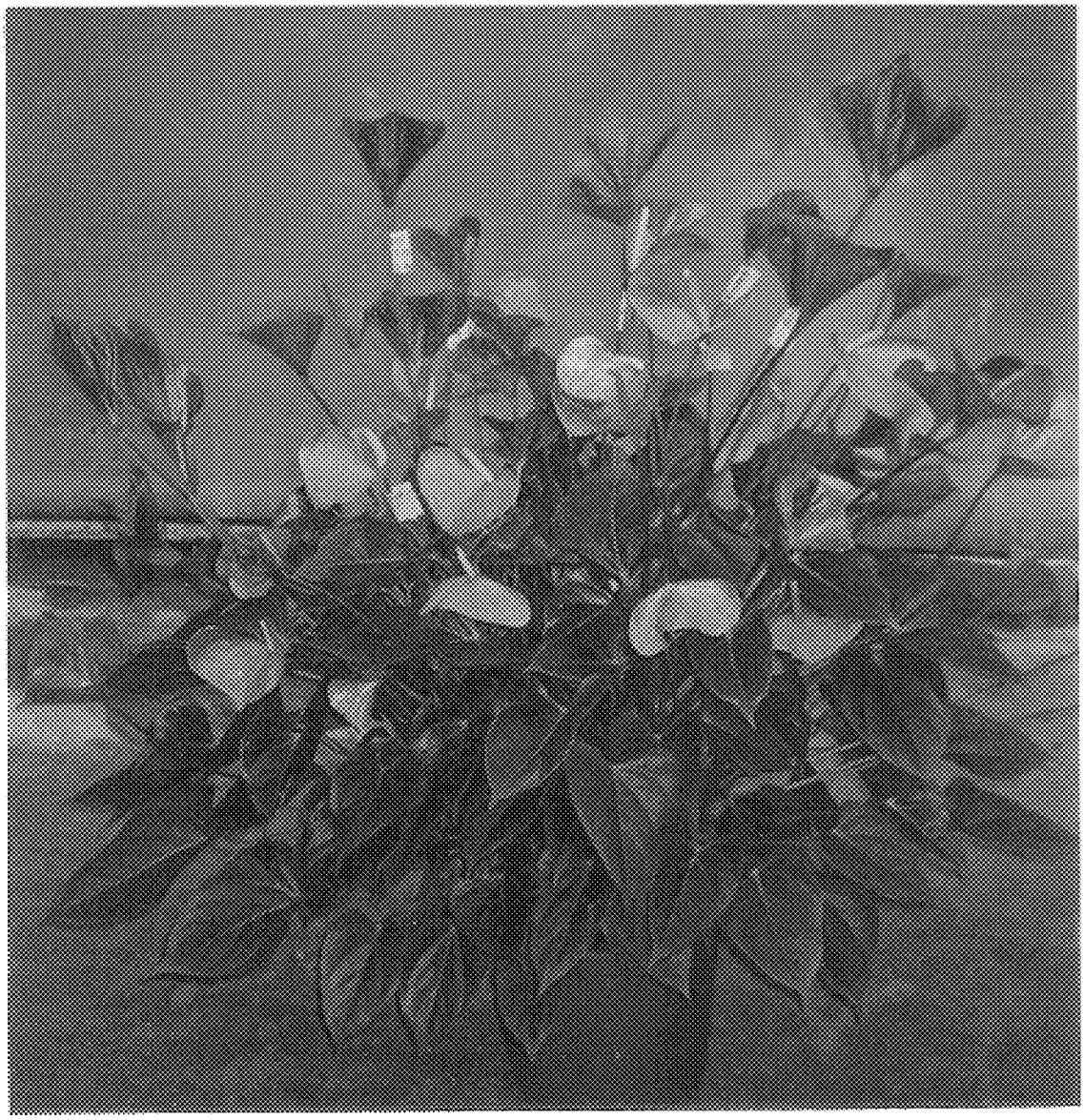

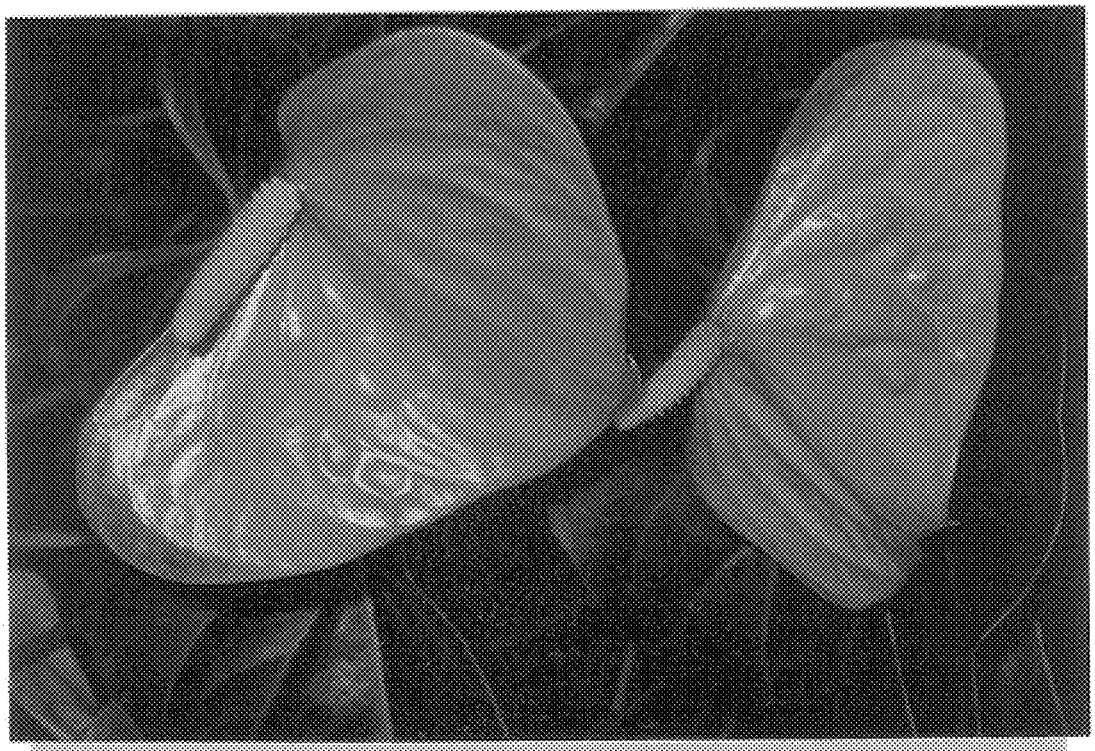
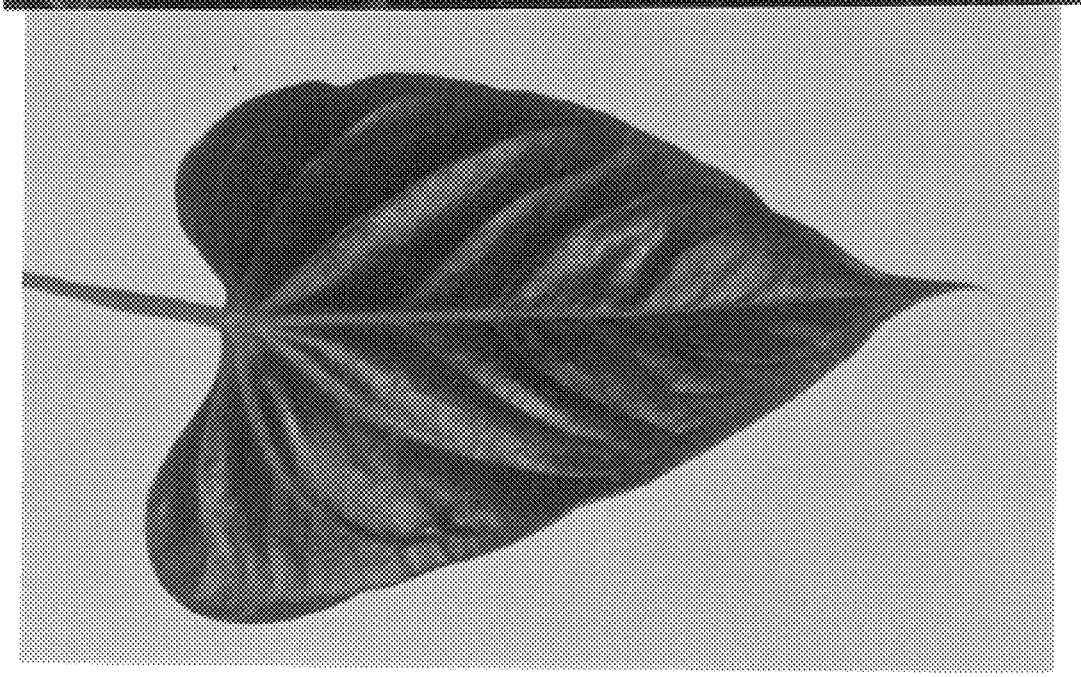

* * * * *